US006328982B1

(12) United States Patent
Shiroyama et al.

(10) Patent No.: US 6,328,982 B1
(45) Date of Patent: Dec. 11, 2001

(54) COOL FEELING COMPOSITION (75) Inventors: Kenichiro Shiroyama; Kiyohito Sawano; Hideaki Ohta, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/366,721

(22) Filed: Aug. 4, 1999

(30) Foreign Application Priority Data

Aug. 4, 1998 (JP) .................................................. 10-220145

(51) Int. Cl.$^7$ ................ A61K 6/00; A61K 7/00
(52) U.S. Cl. .................... 424/401; 424/400; 568/300; 568/579
(58) Field of Search ..................... 424/400, 401; 568/300, 579

(56) References Cited

FOREIGN PATENT DOCUMENTS

| 63-208505 | 8/1988 | (JP) | ............................... A61K/7/00 |
| 63-264522 | 11/1988 | (JP) | ............................... A61K/31/08 |
| 6-107527 | 4/1994 | (JP) | ............................... A61K/7/075 |
| 7-228887 | 8/1995 | (JP) | ............................... C11B/9/00 |
| 9702273 | * 1/1923 | (WO) . | |

* cited by examiner

*Primary Examiner*—Dameron L. Jones
(74) *Attorney, Agent, or Firm*—Sughrue Mion, PLLC (57) ABSTRACT

A cool feeling composition having an excellent cool feeling is obtained by blending at least one cool feeling agent selected from the group consisting of l-menthol, l-isopulegol, 3-(l-menthoxy)propane-1,2-diol and p-menthane-3,8-diol with vanillyl butyl ether. In this cool feeling composition, vanillyl butyl ether is preferably used in an amount, on the weight basis, 1/1000 to 2 times as much as l-menthol, or 1/1000 to 1/2 time as much as l-isopulegol, 3-(l-menthoxy)propane-1,2-diol and p-menthane-3,8-diol. The cool feeling composition is capable of imparting a long-lasting and strong cool feeling when used in cosmetics, toiletries, cataplasms, bath agents, pharmaceutical compositions, etc.

12 Claims, 6 Drawing Sheets

COMPARISON OF COOL FEELING STRENTGTHS OF COMPOSITION CONTAINING VBE AND CAPSICUM TINCTURE

STRONGER COOL FEELING ACHIEVED BY COMPOSITION CONTAINING CAPSICUM TINCTURE | STRONGER COOL FEELING ACHIEVED BY COMPOSITION CONTAINING VBE

FIG. 9

COMPARISON OF COOL FEELING STRENTGTHS OF DEODORANT LOTIONS

STRONGER COOL FEELING ACHIEVED BY VBE-FREE PRODUCT | STRONGER COOL FEELING ACHIEVED BY VBE-CONTAINING PRODUCT

COOL FEELING COMPOSITION

FIELD OF THE INVENTION

This invention relates to a cool feeling composition, which is to be used in various products such as cosmetics, toiletries, cataplasms, bath agents and pharmaceutical compositions and exhibits a long-lasting and strong cool feeling.

BACKGROUND OF THE INVENTION

With the recent drastic changes in consumer' life style and needs, there arises a trend toward various products (cosmetics, toiletries, cataplasms, bath agents, pharmaceutical compositions, etc.) having not only the inherent functions thereof but also an additional effect of providing a refresh feeling during or after using. Accordingly, there have been widely marketed products capable of imparting an additional effect of providing a refreshing feel during or after using. Such products with a need for a refreshing feel are typified by cosmetics to be used in summer, toiletries such as shampoos, cataplasms, bath agents, insect-repellent sprays, etc.

To satisfy the requirement as described above, these products contain various cool feeling agents exemplified by l-menthol, camphor, eugenol, methyl salicylate, menthyl malonate, borneol, cineol, menthone, spearmint, peppermint, l-isopulegol, 3-(l-menthoxy) propane-1,2-diol, p-menthane-3,8-diol, l-menthyl-3-hydroxybutyrate, glycosyl-mono-menthyl-o-acetate, etc.

To satisfy the increasing demand on the market for these cool feeling agents, there has been performed research and development to provide novel cool feeling agents. Also, attempts have been made to enhance an improved cool feeling by combining two or more cool feeling agents or combining cool feeling agents with other substances and to improve the cool feeling or feel in using by examining the compatibility of cool feeling agents with various components in the products. For example, it is known to use 3-(l-menthoxy)propane-1,2-diol together with a specific glyceryl ether (JP-A-63-208505; the term "JP-A" as used herein means an "unexamined published Japanese patent application") or to use 3-(l-menthoxy)propane-1,2-diol together with a hydrophilic polyether-denatured silicone (JP-A-63-264522). However, none of the known cool feeling agents as described above can achieve a satisfactorily strong and long-lasting cool feeling.

As a method for improving the cool feeling strength and persistence, JP-A-6-107527 proposes a hair wash composition with the combined use of a specific cool feeling agent and a specific warm feeling agent. Although this composition shows a somewhat elevated cool feeling effect, the thus obtained effect is still unsatisfactory. It is therefore required to develop a cool feeling agent capable of showing further improved cool feeling strength and cool feeling persistence.

SUMMARY OF THE INVENTION

Accordingly, an object of the present invention is to provide a cool feeling composition which is superior in cool feeling strength and cool feeling persistence to the cool feeling agents proposed conventionally.

Another object of the present invention is to provide a cool feeling composition which shows a high compatibility when used in various products (cosmetics, toiletries, cataplasms, bath agents, pharmaceutical compositions, etc.) and is excellent in cool feeling strength and cool feeling persistence.

Another object of the present invention is to provide a cool feeling composition with a long-lasting effect capable of imparting an excellent refreshing feel to various products (cosmetics, toiletries, cataplasms, bath agents, pharmaceutical compositions, etc.) during or after using.

Another object of the present invention is to provide various products (cosmetics, toiletries, cataplasms, bath agents, pharmaceutical compositions, etc.) which are excellent in cool feeling strength and cool feeling persistence.

To solve the above-described problems, the present inventors have conducted intensive studies. As a result, they have found that a cool feeling composition having a cool feeling strength 2 to 5 times higher than that of the conventional products and a cool feeling persistence 2 to 10 times longer than that of the conventional ones can be obtained by blending vanillyl butyl ether with a specific cool feeling agent, thus completing the present invention.

Accordingly, the present invention provides a cool feeling composition comprising: (a) at least one cool feeling agent selected from the group consisting of l-menthol, l-isopulegol, 3-(l-menthoxy)propane-1,2-diol and p-menthane-3,8-diol; and (b) vanillyl butyl ether.

DETAILED DESCRIPTION OF THE INVENTION

As described above, l-menthol, l-isopulegol, 3-(l-menthoxy)propane-1,2-diol (JP-B-61-48813; the term "JP-B" as used herein means an "examined Japanese patent application") and p-menthane-3,8-diol to be used as a cool feeling agent in the above cool feeling composition are each publicly known as a cool feeling agent. On the other hand, vanillyl butyl ether is publicly known too as a warm feeling agent (JP-B-61-9293).

In the above-described cool feeling composition according to the present invention, vanillyl butyl ether is employed at such a ratio to the cool feeling agent to exert no warm feeling effect. In general, vanillyl butyl ether is used in an amount, on a weight basis, $1/1000$ to 2 times as much as l-menthol, or $1/1000$ to $1/2$ time as much as l-isopulegol, 3-(l-menthoxy)propane-1,2-diol and p-menthane-3,8-diol. Preferably, vanillyl butyl ether is used in an amount, on a weight basis, $1/200$ to 1 time as much as l-menthol, $1/200$ to $1/3$ times as much as l-isopulegol and 3-(l-menthoxy)propane-1,2-diol, or $1/1000$ to $1/3$ times as much as p-menthane-3,8-diol. In the most desirable case, vanillyl butyl ether (VBE) is used at the following weight ratio to each cool feeling agent (referred to as 1.00).

| Cool feeling agent | Optimum VBE rate |
| --- | --- |
| l-menthol | 0.01–1.00 |
| 3-(l-menthoxy)propane-1,2-diol | 0.01–0.05 |
| l-isopulegol | 0.01–0.05 |
| p-menthane-3,8-diol | 0.001–0.01. |

Considering the cool feeling strength of each cool feeling agent as shown below by referring to the cool feeling established by l-menthol as 1.0, the above-described optimum rates seemingly depend on the cool feeling strength of each cool feeling agent.
(Cool feeling strength is determined by referring to the cool feeling strength of l-menthol as 1.0)

| Cool feeling agent | Cool feeling strength |
| --- | --- |
| 3-(l-menthoxy)propane-1,2-diol | 0.20–0.25 |
| l-isopulegol | 0.20–0.30 |
| p-menthane-3,8-diol | 0.10–0.12. |

In a vaseline ointment, 3-(l-menthoxy)propane-1,2-diol shows a cool feeling 2.0 to 2.5 times stronger than that of l-menthol.

When two or more agents selected from among l-menthol, l-isopulegol, 3-(l-menthoxy) propane-1,2-diol and p-menthane-3,8-diol are used simultaneously as cool feeling agents, the content of vanillyl butyl ether is determined by taking the preferable ratios thereof to each of these cool feeling agents into consideration.

It is preferable that the content of vanillyl butyl ether in the final product at using is not more than 0.25% by weight. This is because when the content of vanillyl butyl ether in the final product at using exceeds 0.25% by weight, a warm feeling effect is established in general regardless of the content of the cool feeling agents.

Although the present inventors tried to improve the cool feeling effect by combining various cool feeling agents other than l-menthol, l-isopulegol, 3-(l-menthoxy)propane-1,2-diol and p-menthane-3,8-diol with various warm feeling agents other than vanillyl butyl ether, no combination but those employed in the present invention can establish any satisfactory effect as far as they examined. That is to say, they have surprisingly found that the combinations of the substances according to the present invention can selectively achieve very favorable effects.

The cool feeling composition of the present invention may optionally contain cool feeling agents other than l-menthol, l-isopulegol, 3-(l-menthoxy)propane-1,2-diol and p-menthane-3,8-diol and warm feeling agents other than vanillyl butyl ether, so long as the effects of the present invention are not deteriorated thereby.

The cool feeling composition according to the present invention can be used in various products to which a cool feeling effect is to be imparted. Examples of the products to which the cool feeling composition of the present invention can be added include cosmetics such as various lotions/essences (softening lotions, astringent lotions, cleansing lotions, calamine lotions, after shave lotions, makeup transparent lotions, skin lotions, etc.), facial cosmetics such as creams/milky lotions (massage creams, cleansing creams, skin creams, foundation creams for summer, suntan creams, milky lotions, lip creams, etc.), colognes such as perfumes and eau de cologne, lipsticks and deodorant agents; toiletries such as shampoos, conditioners, hair tonics, hair gels, hair growth stimulants, facial cleansers, body soaps, shaving foams, shaving creams, face soaps and hair rinses; household goods such as various bath agents (powders, liquids, bubbling tablets, etc.); and phannaceutical compositions such as insect-repellent sprays, insect-repellent lotions, hair tonics, cataplasms, analgesic preparations (lotions, sprays, etc.). In addition, fabric, etc., may be impregnated with the cool feeling composition of the present invention to give, for example, a moist hot hand towel capable of giving a refreshing feel.

From another point of view, the products in which the cool feeling composition of the present invention is usable include external preparations specified in the Pharmaceutical Affairs Law (aerosols, suspensions/emulsions, plasters, ointments, cataplasms, liniments, lotions, etc.) and cosmetics specified in accordance with class approval standards (cleansing cosmetics, hair cosmetics, basic cosmetics, aromatic cosmetics, suntan/sunscreen goods, lip cosmetics, bathing preparations, etc.).

Needless to say, the products in which the cool feeling composition of the present invention is usable are not restricted to the products or forms as stated above. That is to say, the cool feeling composition of the present invention is appropriately applicable to any products usually containing cool feeling agents.

The content of the cool feeling composition of the present invention in a product widely varies depending on the amount of the product at a single use, the style of the product (i.e., to be used as such or sprayed as in the case of an aerosol), the form thereof (i.e., liquid or solid), etc. In general, the content of the cool feeling composition ranges from 0.001 to 20% by weight, preferably from 0.01 to 10% by weight, of the whole product composition. However, the cool feeling composition of the present invention may be added to a product in an arbitrary amount without restriction so as to establish the effects of the present invention. The cool feeling composition may be added as the composition to the product. Alternatively, the cool feeling agent and the warm feeling agent may be separately added to the product in such a manner as to give a composition ratio falling within the scope of the present invention. When the cool feeling agent and the warm feeling agent are added separately, the resultant products are involved in the scope of the present invention so long as at least one cool feeling agent selected from the group consisting of l-menthol, l-isopulegol, 3-(l-menthoxy)propane-1,2-diol and p-menthane-3,8-diol, and vanillyl butyl ether are employed at the same time.

EXAMPLES

The present invention will be described in greater detail by reference to the following Examples and Comparative Examples, but it should be understood that the invention is not construed as being limited thereto. Unless otherwise noted, all percentages are by weight.

Example 1 and Comparative Example 1

Figure 1:
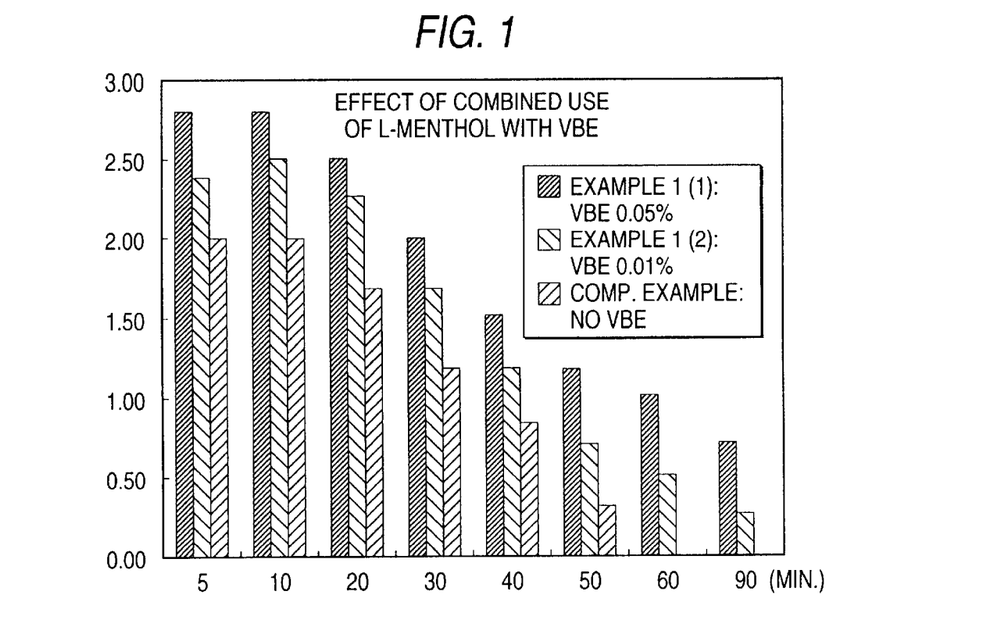
FIG. 1 is a graph showing changes in cool feeling strengths with the passage of time of l-menthol-containing cool feeling compositions containing 0.05%, 0.01% or 0% of vanillyl butyl ether (VBE).

500 μliter portions of samples containing l-menthol and vanillyl butyl ether at the composition ratios (%) as specified in the formulation example 1 given below were each dropped onto a patch (37.5 mm×50 mm manufactured by Towa Yakuhin Kogyo) and applied to the forearm. Then the cool feeling thus achieved was evaluated with the passage of time based on the following criteria. Table 1 and FIG. 1 show the evaluation data expressed in the average of scores provided by 5 skilled panelists.

Evaluation data of formulation example 1:

TABLE 1

| Time (min) | 5 | 10 | 20 | 30 | 40 | 50 | 60 | 90 |
|---|---|---|---|---|---|---|---|---|
| Ex. 1 (1) | 2.80 | 2.80 | 2.50 | 2.00 | 1.50 | 1.16 | 1.00 | 0.70 |
| Ex. 1 (2) | 2.38 | 2.50 | 2.25 | 1.67 | 1.17 | 0.70 | 0.50 | 0.25 |
| Comp. Ex. 1 | 2.00 | 2.00 | 1.67 | 1.17 | 0.83 | 0.30 | 0.00 | 0.00 |

Example 2 and Comparative Example 2

Figure 2:
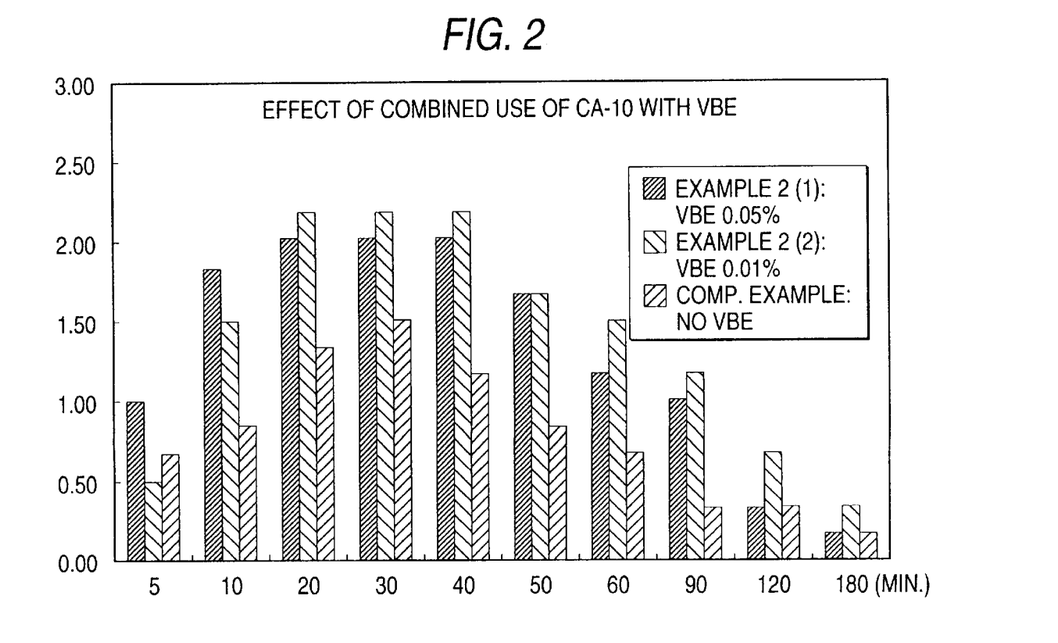
FIG. 2 is a graph showing changes in cool feeling strengths with the passage of time of 3-(l-menthoxy) propane-1,2-diol (CA-10)-containing cool feeling compositions containing 0.05%, 0.01% or 0% of vanillyl butyl ether (VBE).

500 μliter portions of samples containing 3-(l-menthoxy)propane-1,2-diol and vanillyl butyl ether at the composition ratios (%) as specified in the formulation example 2 given below were each dropped onto a patch (37.5 mm×50 mm manufactured by Towa Yakuhin Kogyo) and applied to the forearm. Then the cool feeling thus achieved was evaluated with the passage of time based on the same criteria as in EXAMPLE 1. Table 2 and FIG. 2 show the evaluation data expressed in the average of scores provided by 5 skilled panelists.

| Formulation Ex. 2 | Ex. 2(1) | Ex. 2(2) | Comp. Ex. 2 |
|---|---|---|---|
| 95% ethanol | 40.00 | 40.00 | 40.00 |
| CA-10 | 2.00 | 2.00 | 2.00 |
| vanillyl butyl ether | 0.05 | 0.01 | — |
| purified water | 57.95 | 57.99 | 58.00 |
|  | 100.00 | 100.00 | 100.00. |

(In the above formulation, CA-10 stands for 3-(l-menthoxy)propane-1,2-diol.)

Evaluation data of formulation example 2:

TABLE 2

| Time (min) | 5 | 10 | 20 | 30 | 40 | 50 | 60 | 90 | 120 | 190 |
|---|---|---|---|---|---|---|---|---|---|---|
| Ex. 1 (1) | 1.00 | 1.83 | 2.00 | 2.00 | 2.00 | 1.67 | 1.17 | 1.00 | 0.33 | 0.17 |
| Ex. 1 (2) | 0.50 | 1.50 | 2.17 | 2.17 | 2.17 | 1.67 | 1.50 | 1.17 | 0.67 | 0.33 |
| Comp. Ex. 1 | 0.67 | 0.83 | 1.33 | 1.50 | 1.17 | 0.83 | 0.67 | 0.33 | 0.33 | 0.17 |

Evaluation criteria:

| | |
|---|---|
| 3 | Very strong cool feeling. |
| 2 | Strong cool feeling. |
| 1 | Cool feeling. |
| 0 | No cool feeling. |
| −1 | Warm feeling. |

Example 3 and Comparative Example 3

Figure 3:
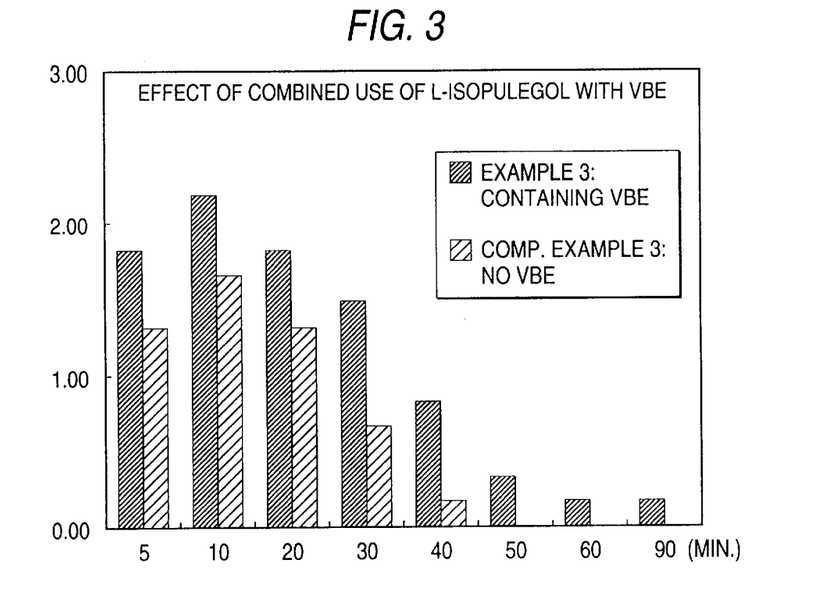
FIG. 3 is a graph showing changes in cool feeling strengths with the passage of time of l-isopulegol-containing cool feeling compositions containing 0.01% or 0% of vanillyl butyl ether (VBE).

500 μliter portions of samples containing l-isopulegol and vanillyl butyl ether at the composition ratios (%) as specified in the formulation example 3 given below were each droppedontoapatch (37.5 mm×50mmmanufacturedby Towa Yakuhin Kogyo) and applied to the forearm. Then the cool feeling thus achieved was evaluated with the passage of time based on the same criteria as in EXAMPLE 1. Table 2 and FIG. 3 show the evaluation data expressed in the average of scores provided by 5 skilled panelists.

| Formulation Ex. 1 | Ex. 1(1) | Ex. 1(2) | Comp. Ex. 1 |
|---|---|---|---|
| 95% ethanol | 40.00 | 40.00 | 40.00 |
| l-menthol | 0.50 | 0.50 | 0.50 |
| vanillyl butyl ether | 0.05 | 0.01 | — |
| purified water | 59.45 | 59.49 | 59.50 |
|  | 100.00 | 100.00 | 100.00. |

| Formulation Ex. 3 | Ex. 3 | Comp. Ex. 3 |
|---|---|---|
| 95% ethanol | 40.00 | 40.00 |
| l-isopulegol | 2.00 | 2.00 |

-continued

| Formulation Ex. 3 | Ex. 3 | Comp. Ex. 3 |
|---|---|---|
| vanillyl butyl ether | 0.01 | — |
| purified water | 57.99 | 58.00 |
| | 100.00 | 100.00. |

Evaluation data of formulation example 3:

TABLE 3

| Time (min) | 5 | 10 | 20 | 30 | 40 | 50 | 60 | 90 |
|---|---|---|---|---|---|---|---|---|
| Ex. 3 | 1.83 | 2.17 | 1.83 | 1.50 | 0.83 | 0.33 | 0.17 | 0.17 |
| Comp. Ex. 3 | 1.33 | 1.67 | 1.33 | 0.67 | 0.17 | 0.00 | 0.00 | 0.00 |

Example 4 and Comparative Example 4

Figure 4:
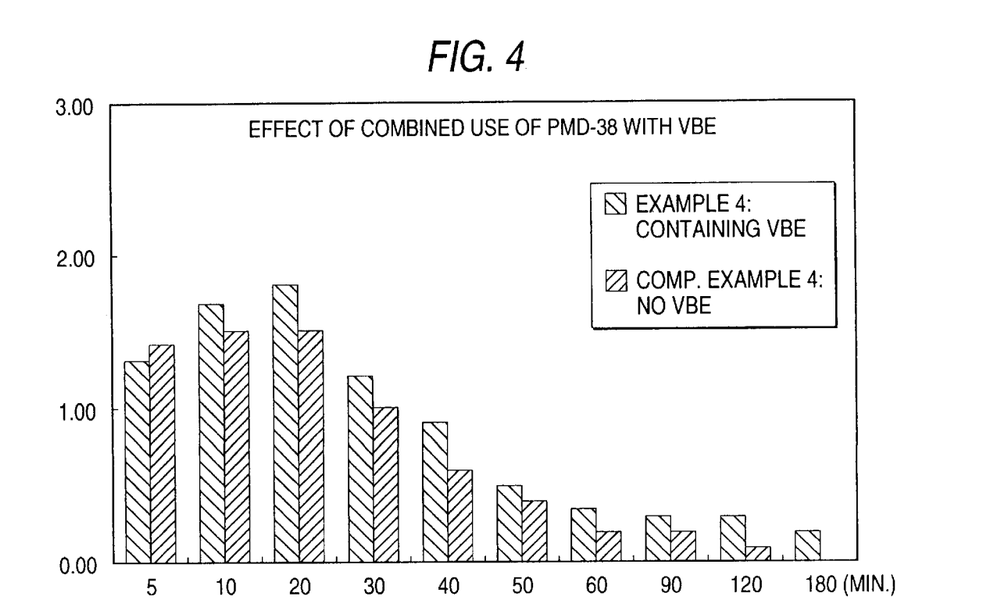
FIG. 4 is a graph showing changes in cool feeling strengths with the passage of time of p-menthane-3,8-diol (PMD-38)-containing cool feeling compositions containing 0.01% or 0% of vanillyl butyl ether (VBE).

500 μliter portions of samples containing p-menthane-3,8-diol and vanillyl butyl ether at the composition ratios (%) as specified in the formulation example 4 given below were each dropped onto a patch (37.5 mm×50 mm manufactured by Towa Yakuhin Kogyo) and applied to the forearm. Then the cool feeling thus achieved was evaluated with the passage of time based on the same criteria as in EXAMPLE 1. Table 4 and FIG. 4 show the evaluation data expressed in the average of scores provided by 5 skilled panelists.

| Formulation Ex. 4 | Ex. 4 | Comp. Ex. 4 |
|---|---|---|
| 95% ethanol | 40.00 | 40.00 |
| PMD-38 | 2.00 | 2.00 |
| vanillyl butyl ether | 0.01 | — |
| purified water | 57.99 | 58.00 |
| | 100.00 | 100.00. |

(In the above formulation, PMD-38 stands for p-menthane-3,8-diol.)

Evaluation data of formulation example 4

TABLE 4

| Time (min) | 5 | 10 | 20 | 30 | 40 | 50 | 60 | 90 | 120 | 180 |
|---|---|---|---|---|---|---|---|---|---|---|
| Ex. 4 | 1.30 | 1.67 | 1.80 | 1.20 | 0.90 | 0.50 | 0.35 | 0.30 | 0.30 | 0.20 |
| Comp. Ex. 4 | 1.40 | 1.50 | 1.50 | 1.00 | 0.60 | 0.40 | 0.20 | 0.20 | 0.10 | 0.00 |

When the cool feeling agents were used together with vanillyl butyl ether, the most remarkable effect was achieved by the combined use of 3-(l-menthoxy)propane-1,2-diol (CA-10) with vanillyl butyl ether (VBE) at the following formulation. Next, the evaluation method and the results thereof will be described.

Formulation

| Component | with VBE | CA-10 alone |
|---|---|---|
| 95% ethanol | 40.00 | 40.00 |
| CA-10 | 2.00 | 2.00 |
| vanillyl butyl ether | 0.01 | — |
| purified water | 57.99 | 58.00 |
| | 100.00 | 100.00. |

Figure 5:
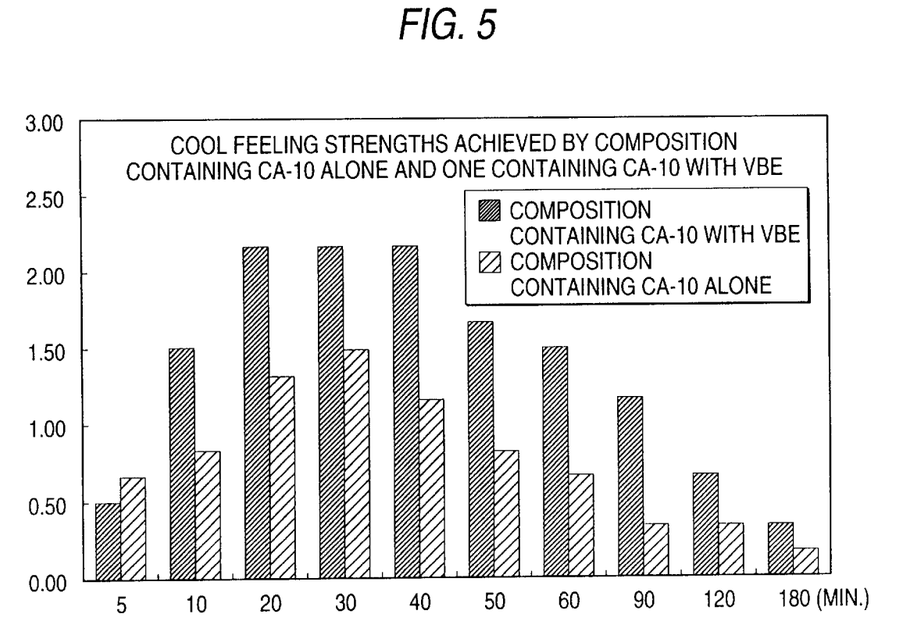
FIG. 5 is a graph showing changes in cool feeling strengths with the passage of time of 3-(l-menthoxy) propane-1,2-diol (CA-10)-containing cool feeling compositions containing 0.01% or 0% of vanillyl butyl ether (VBE).

Evaluation method 1: Cool feelings of preparation containing CA-10 alone and one with the combined use of VBE By using the same evaluation method and criteria as those of Example 2, cool feeling was evaluated with the passage of time. Table 5 and FIG. 5 show the evaluation data expressed in the average of scores provided by 5 skilled panelists. Evaluation data (Cool feelings of preparation containing CA-10 alone and one with the combined use of VBE)

TABLE 5

| Time (min) | 5 | 10 | 20 | 30 | 40 | 50 | 60 | 90 | 120 | 180 |
|---|---|---|---|---|---|---|---|---|---|---|
| With VBE (0.01%) | 0.50 | 1.50 | 2.17 | 2.17 | 2.17 | 1.67 | 1.50 | 1.17 | 0.67 | 0.33 |
| CA-10 alone | 0.67 | 0.83 | 1.33 | 1.50 | 1.17 | 0.83 | 0.67 | 0.33 | 0.33 | 0.17 |

Evaluation method 2: (Comparison in cool feeling strength of preparation containing CA-10 alone and one with the combined use of VBE)

Figure 6:
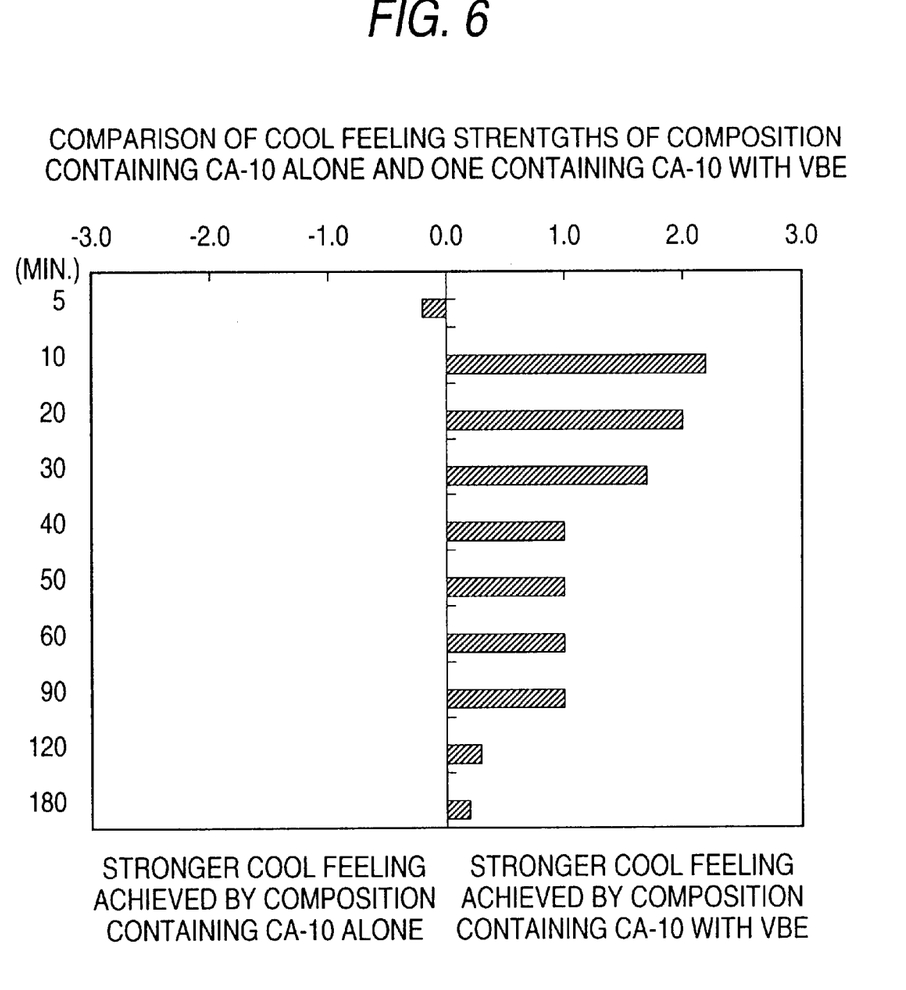
FIG. 6 is a graph showing a comparison in cool feeling strengths with the passage of time of a 3-(l-menthoxy) propane-1,2-diol (CA-10)-containing cool feeling composition containing 0.01% of vanillyl butyl ether (VBE) with a 3-(l-menthoxy)propane-1,2-diol (CA-10)-containing cool feeling composition containing 0% of VBE.

500 μliter portions of samples containing 3-(l-menthoxy)propane-1,2-diol and vanillyl butyl ether at the composition ratios (%) as specified in the above-described formulation were each dropped onto a patch (37.5 mm×50 mm manufactured by Towa Yakuhin Kogyo) and applied to the forearm. Then the cool feeling thus achieved was evaluated with the passage of time based on the following criteria. Table 6 and FIG. 6 show the evaluation data expressed in the average of scores provided by 5 skilled panelists.

Evaluation criteria:

| | |
|---|---|
| 3 | Much stronger cool feeling achieved by the preparation with the combined use of VBE. |
| 2 | Stronger cool feeling achieved by the preparation with the combined use of VBE. |
| 1 | Cool feeling achieved by the preparation with the combined use of VBE. |
| 0 | No difference in cool feeling. |
| −1 | Cool feeling achieved by the preparation containing CA-10 alone. |
| −2 | Stronger cool feeling achieved by the preparation containing CA-10 alone. |
| −3 | Much stronger cool feeling achieved by the preparation containing CA-10 alone. |

TABLE 6

| Time (min) | 5 | 10 | 20 | 30 | 40 | 50 | 60 | 90 | 120 | 180 |
|---|---|---|---|---|---|---|---|---|---|---|
| Comparison in cool feeling strength | −0.2 | 2.2 | 2.0 | 1.7 | 1.0 | 1.0 | 1.0 | 1.0 | 0.3 | 0.2 |

Example 5 and Comparative Example 5

Figure 7:
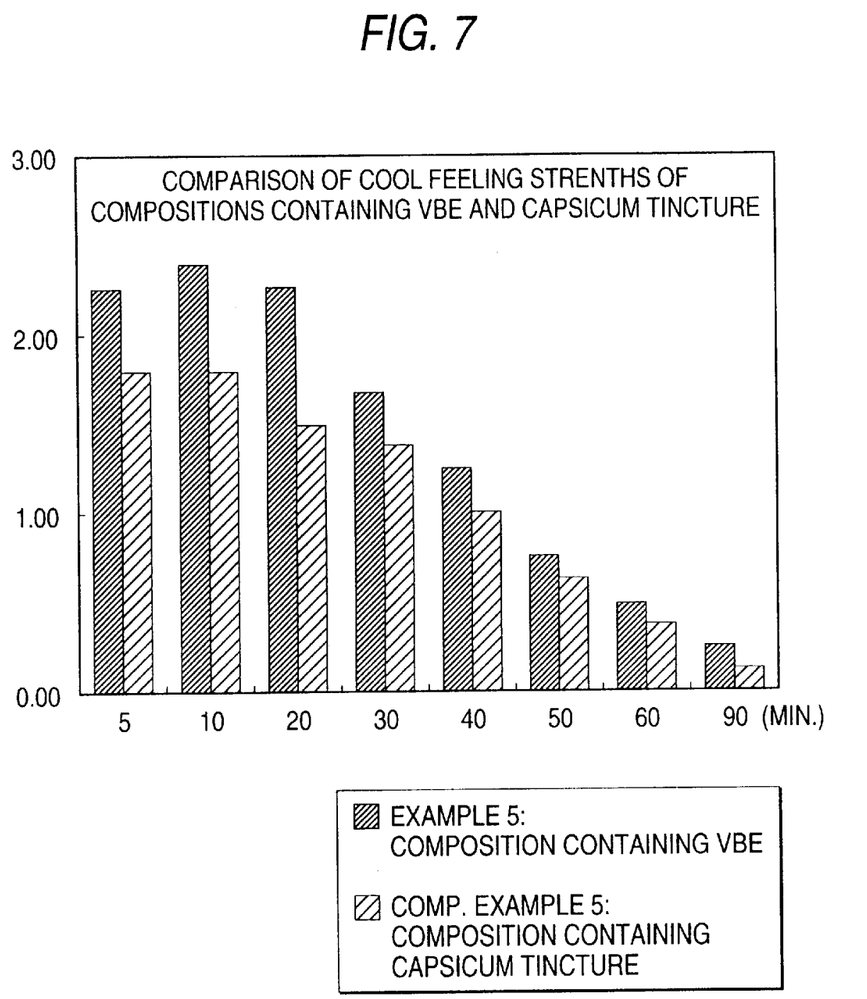
FIG. 7 is a graph showing changes in cool feeling strengths with the passage of time of l-menthol-containing cool feeling compositions containing 0.01% of vanillyl butyl ether (VBE) or 0.01% of capsicum tincture.
Figure 8:
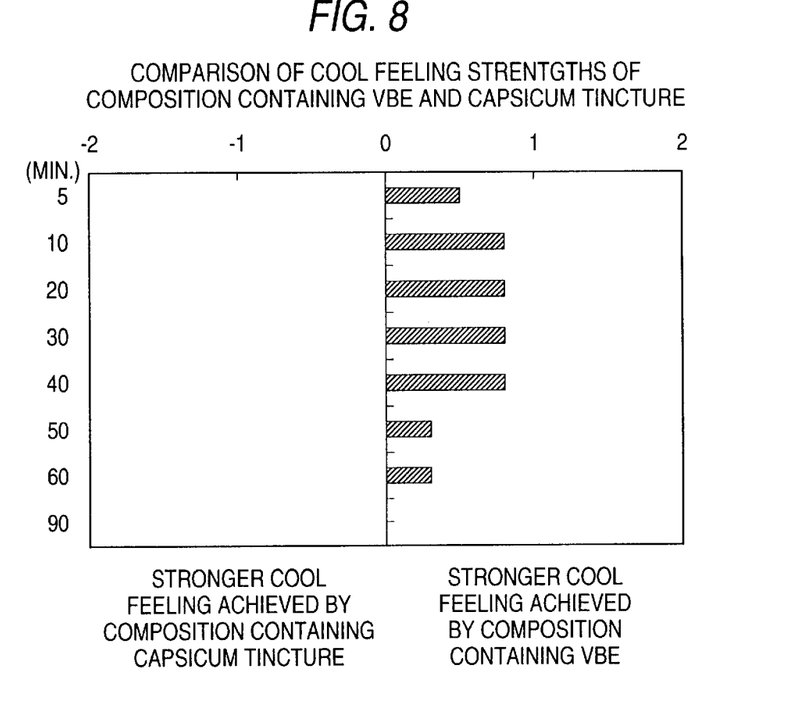
FIG. 8 is a graph showing a comparison in cool feeling strengths with the passage of time of an l-menthol-containing cool feeling composition containing 0.01% of vanillyl butyl ether (VBE) with an l-menthol-containing cool feeling composition containing 0.01% of capsicum tincture.

A typical warm feeling agent capsicum tincture was added to l-menthol and the cool feeling effect thus achieved was compared with the cool feeling obtained by adding vanillyl butyl ether. 500 μl portions of samples prepared at the composition ratios (%) as specified in the formulation example 5 given below were each dropped onto a patch (37.5 mm×50 mm manufactured by Towa Yakuhin Kogyo) and applied to the forearm. Then the cool feeling thus achieved was evaluated with the passage of time based on the criteria 1 and 2 as specified below. Table 7 and FIG. 7 show the evaluation data obtained on the basis of the criteria 1, while Tables 8 and FIG. 8 show the evaluation data obtained on the basis of the criteria 2. These data are expressed in the average of scores provided by 5 skilled panelists.

| Formulation Ex. 5 | Ex. 5 | Comp. Ex. 5 |
|---|---|---|
| l-menthol | 0.50 | 0.50 |
| vanillyl butyl ether | 0.01 | — |
| capsicum tincture | — | 0.01 |
| 95% ethanol | 40.00 | 40.00 |
| NIKKOL HCO-40 | 0.50 | 0.50 |
| purified water | 58.99 | 58.99 |
| | 100.00 | 100.00. |

(In the above formulation, NIKKOL HCO-40 stands for PEG-40 hydrogenated castor oil).

Evaluation criteria 1:

| | |
|---|---|
| 3 | Very strong cool feeling. |
| 2 | Strong cool feeling. |
| 1 | Cool feeling. |
| 0 | No cool feeling. |
| −1 | Warm feeling. |

Evaluation data 1: (Cool feeling of preparation obtained by adding VBE to l-menthol and one obtained by adding capsicum tincture to l-menthol)

TABLE 7

| Time (min) | 5 | 10 | 20 | 30 | 40 | 50 | 60 | 90 |
|---|---|---|---|---|---|---|---|---|
| Ex. 5 | 2.25 | 2.38 | 2.25 | 1.67 | 1.25 | 0.75 | 0.50 | 0.25 |
| Comp. Ex. 5 | 1.80 | 1.80 | 1.50 | 1.38 | 1.00 | 0.63 | 0.38 | 0.13 |

Evaluation criteria 2:

| | |
|---|---|
| 2 | Stronger cool feeling achieved by the preparation with the use of VBE. |
| 1 | Somewhat stronger cool feeling achieved by the preparation with the use of VBE. |
| 0 | Comparable. |
| −1 | Somewhat stronger cool feeling achieved by the preparation with the use of capsicum tincture. |
| −2 | Stronger cool feeling achieved by the preparation with the use of capsicum tincture. |

Evaluation data 2: (Comparison in cool feeling strength of preparation obtained by adding VBE to l-menthol and one obtained by adding capsicum tincture to l-menthol)

TABLE 8

| Time (min) | 5 | 10 | 20 | 30 | 40 | 50 | 60 | 90 |
|---|---|---|---|---|---|---|---|---|
| Comparison in cool feeling strength | 0.5 | 0.8 | 0.8 | 0.8 | 0.8 | 0.3 | 0.3 | 0.0 |

Example 6 and Comparative Example 6

Figure 9:
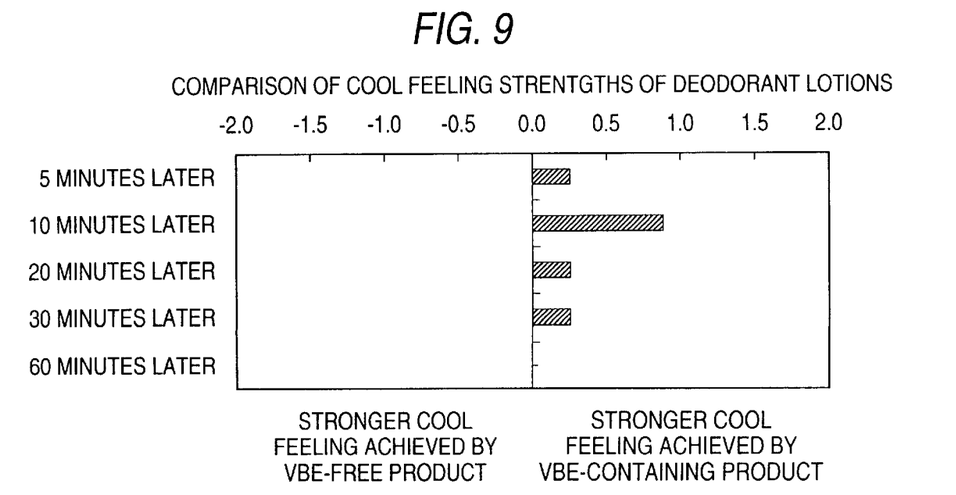
FIG. 9 is a graph showing a comparison in cool feeling strengths with the passage of time of an l-menthol-containing deodorant lotion containing vanillyl butyl ether (VBE) with an l-menthol-containing deodorant lotion free from VBE.

Deodorant lotions of the following formulation were prepared and used by 8 female panelists. The test was performed by applying a lotion containing vanillyl butyl ether and one free form vanillyl butyl ether were applied in the same amount respectively to left and right forearms and the cool feelings were compared after 5, 10, 20, 30 and 60 minutes. Table 9 and FIG. 9 show the results.

Evaluation criteria:

| | |
|---|---|
| 3 | Much stronger cool feeling achieved by the lotion containing VBE. |
| 2 | Stronger cool feeling achieved by the lotion containing VBE. |
| 1 | Somewhat stronger cool feeling achieved by the lotion containing VBE. |
| 0 | Comparable. |
| −1 | Somewhat stronger cool feeling achieved by the VBE-free lotion. |
| −2 | Stronger cool feeling achieved by the VBE-free lotion. |
| −3 | Much stronger cool feeling achieved by the VBE-free lotion. |

| Formulation Ex. 6 | Ex. 6 | Comp. Ex. 6 |
|---|---|---|
| perfume | 0.300 | 0.300 |
| l-menthol | 0.100 | 0.100 |
| vanillyl butyl ether | 0.005 | — |
| NIKKOL HCO-40 | 0.500 | 0.500 |
| triclosan | 0.100 | 0.100 |

-continued

| Formulation Ex. 6 | Ex. 6 | Comp. Ex. 6 |
|---|---|---|
| magnesia/silica powder | 1.000 | 1.000 |
| methylparaben | 0.100 | 0.100 |
| butylene glycol | 1.000 | 1.000 |
| 95% ethyl alcohol | 45.000 | 45.000 |
| purified water | 51.895 | 51.900 |
| | 100.000 | 100.000. |

Evaluation data of deodorant lotions:

TABLE 9

| Panelist/Time (min) | 5 | 10 | 20 | 30 | 60 |
|---|---|---|---|---|---|
| F-1 | 2 | 2 | 0 | 0 | 0 |
| F-2 | 0 | 1 | 0 | 0 | 0 |
| F-3 | −1 | −1 | 0 | 0 | −1 |
| F-4 | 0 | 3 | 1 | 1 | 1 |
| F-5 | 2 | 3 | 0 | 0 | 0 |
| F-6 | 0 | −1 | 0 | 0 | 0 |
| F-7 | −1 | 0 | 0 | 0 | −1 |
| F-8 | 0 | 2 | 1 | 1 | 1 |
| Average score | 0.25 | 0.875 | 0.25 | 0.25 | 0 |

As Tables 1 to 9 and FIGS. 1 to 9 showing the evaluation data of the above Examples and Comparative Examples clearly indicate, the cool feeling compositions of the present invention are remarkably superior in cool feeling strength and cool feeling persistence to those free from vanillyl butyl ether or those containing warm feeling agents other than vanillyl butyl ether.

Moreover, the cool feeling compositions of the present invention can exert an excellent cool feeling effect when employed in various products. In the following Examples 7 to 12, particular formulation examples of these products will be illustrated.

Example 7
(liquid bath agent)

| (Formulation example) | (%) |
|---|---|
| butylene glycol | 2.00 |
| PEG-40 Hydrogenated Castor oil | 0.75 |
| Polysorbate 80 | 0.75 |
| 95% ethanol | 40.00 |
| CA-10 | 3.00 |
| l-menthol | 3.00 |
| vanillyl butyl ether | 0.50 |
| perfume | 1.00 |
| coloring matter | q.s. |
| purified water suffice to give total amount of | 100.00. |

Example 8
(powdery bath agent)

| (Formulation example) | (%) |
|---|---|
| sodium sulfate | 64.95 |
| Sodium Bicarbonate | 30.00 |
| Silica | 1.00 |
| Yellow Color No. 202 | 0.05 |

-continued

| (Formulation example) | (%) |
|---|---|
| l-menthol | 1.50 |
| vanillyl butyl ether | 1.50 |
| perfume | 1.00 |
| total | 100.00. |

Example 9
(shampoo)

| (Formulation example) | (%) |
|---|---|
| purified water | 41.93 |
| Poiz C-60H *1 | 0.60 |
| Emarl 20C *2 | 40.00 |
| Beaulight A-5000 *3 | 5.00 |
| Swanol AM-101 *4 | 5.00 |
| Amisol CDE *5 | 4.00 |
| glycerin | 0.10 |
| ethylene glycol distearate | 1.50 |
| citric acid | 0.22 |
| potassium chloride | 0.30 |
| methylparaben | 0.20 |
| propylparaben | 0.10 |
| ethylparaben | 0.10 |
| tetrasodium edetate | 0.05 |
| perfume | 0.50 |
| l-menthol | 0.20 |
| vanillyl butyl ether | 0.20 |
| total | 100.00. |

*1 Polyquaternium-10
*2 Sodium Laureth Sulfate (25%)
*3 Disodium Lauramido PEG-5 Sulfosuccinate
*4 Sodium cocoamphoacetate
*5 Cocamide DEA

Example 10
(vaseline ointment)

| (Formulation example) | (%) |
|---|---|
| Petrolactum | 77.49 |
| liquid paraffin | 19.00 |
| cetyl palmitate | 3.00 |
| perfume | 0.30 |
| 3-(l-menthoxy)propane-1,2-diol | 0.20 |
| vanillyl butyl ether | 0.01 |
| total | 100.00. |

Example 11
(deodorant powder spray)

| (Formulation example) | (%) |
|---|---|
| Aluminium Hydroxychloride | 1.00 |
| Silica | 1.00 |
| isopropyl myristate | 2.00 |
| Cyclomethicone | 0.50 |
| sorbitan sesquioleate | 0.10 |
| triclosan | 0.02 |
| l-menthol | 0.30 |
| 3-(l-menthoxy)propane-1,2-diol | 1.50 |

-continued

| (Formulation example) | (%) |
|---|---|
| vanillyl butyl ether | 0.50 |
| perfume | 0.20 |
| 95% ethanol | 3.33 |
| LPG | 90.00 |
| total | 100.00. |

Example 12
(cataplasm)

| (Formulation example) | (%) |
|---|---|
| gelatin | 3.00 |
| polyvinyl alcohol | 2.00 |
| sodium polyacrylate | 2.00 |
| Cellulose Gum | 1.00 |
| glycerin | 25.00 |
| sorbitol | 53.95 |
| l-menthol | 1.50 |
| p-menthane-3,8-diol | 1.50 |
| total | 100.00. |

As described above, the cool feeling composition according to the present invention is excellent in cool feeling strength and cool feeling persistence. When employed in various products (cosmetics, toiletries, cataplasms, bath agents, pharmaceutical compositions, etc.), the cool feeling composition of the present invention can impart excellent cool feeling and refresh feeling to these products, which makes it highly useful industrially.

What is claimed is:

1. A cool feeling composition consisting essentially of: (a) at least one cool feeling agent selected from the group consisting of l-menthol, l-isopulegol, 3-(l-menthoxy) propane-1,2-diol and p-menthane-3,8-diol; and (b) vanillyl butyl ether, wherein vanillyl butyl ether is used in an amount, on a weight basis, $\frac{1}{1000}$ to 2 times as much as l-menthol, or $\frac{1}{1000}$ to $\frac{1}{2}$ time as much as l-isopulegol, 3-(l-menthoxy)propane-1,2-diol or p-menthane-3,8-diol, wherein said vanillyl butyl ether is employed as such a ration to the cool feeling agent to exert no warm feeling effect'.

2. The cool feeling composition as claimed in claim 1, wherein vanillyl butyl ether is used in an amount, on the weight basis, $\frac{1}{200}$ to 1 time as much as l-menthol, $\frac{1}{200}$ to $\frac{1}{3}$ time as much as l-isopulegol and 3-(l-menthoxy)propane-1, 2-diol, or $\frac{1}{1000}$ to $\frac{1}{3}$ time as much as p-menthane-3,8-diol.

3. A cosmetic composition comprising the cool feeling composition as defined in claim 1 in an amount of 0.001 to 20% by weight of the total composition.

4. A toiletry composition comprising the cool feeling composition as defined in claim 1 in an amount of 0.001 to 20% by weight of the total composition.

5. A cataplasm preparation comprising the cool feeling composition as defined in claim 1 in an amount of 0.001 to 20% by weight of the total composition.

6. A bath agent composition comprising the cool feeling composition as defined in claim 1 in an amount of 0.001 to 20% by weight of the total composition.

7. A pharmaceutical composition comprising the cool feeling composition as defined in claim 1 in an amount of 0.001 to 20% by weight of the total composition.

8. A process for providing cool feeling which comprises topically applying the cool feeling composition as defined in claim 1 to human skin.

9. The cool feeling composition as claimed in claim 1, which comprises, as the at least one cool feeling agent, at least one cool feeling agent selected from the group l-isopulegol, 3-(l-menthoxy)propane-1,2-diol or p-menthane-3,8-diol.

10. The cool-feeling composition as claimed in claim 1, wherein the cool-feeling agent is l-isopulegol.

11. The cool-feeling composition as claimed in claim 1, wherein the cool-feeling agent is 3-(l-menthoxy)propane-1, 2-diol.

12. The cool-feeling composition as claimed in claim 1, wherein the cool-feeling agent is p-menthane-3,8-diol.

* * * * *